United States Patent [19]

Weichert et al.

[11] Patent Number: 5,693,672
[45] Date of Patent: *Dec. 2, 1997

[54] 3,4,5-SUBSTITUTED BENZOYLGUANIDINES, PROCESS FOR THEIR PREPARATION, THEIR USE AS A MEDICAMENT OR DIAGNOSTIC AND MEDICAMENT CONTAINING THEM

[75] Inventors: Andreas Weichert, Frankfurt am Main; Hans-Jochen Lang, Hofheim/Taunus; Wolfgang Scholz, Eschborn; Udo Albus, Florstadt; Florian Lang, Markdorf, all of Germany

[73] Assignee: Hoechst Aktiengesellschaft, Frankfurt am Main, Germany

[*] Notice: The term of this patent shall not extend beyond the expiration date of Pat. No. 5,373,024.

[21] Appl. No.: 451,309

[22] Filed: May 26, 1995

Related U.S. Application Data

[63] Continuation of Ser. No. 303,006, Sep. 8, 1994, abandoned, which is a continuation of Ser. No. 83,576, Jun. 30, 1993, abandoned.

[30] Foreign Application Priority Data

Jul. 1, 1992 [DE] Germany .......................... 42 21 594.3
Jul. 22, 1992 [DE] Germany .......................... 42 24 107.3
Dec. 28, 1992 [DE] Germany .......................... 42 44 319.9

[51] Int. Cl.$^6$ .................... C07C 279/22; A61K 31/18; A61K 31/155
[52] U.S. Cl. .................... 514/618; 514/522; 514/603; 514/634; 514/821; 564/86; 564/162; 564/237
[58] Field of Search .................... 564/162, 86, 237; 514/522, 603, 637, 821

[56] References Cited

U.S. PATENT DOCUMENTS

| | | | |
|---|---|---|---|
| 3,247,035 | 4/1966 | Henderson | 562/435 |
| 3,420,874 | 1/1969 | Henderson | 562/435 |
| 3,728,332 | 4/1973 | Tessler et al. | 536/110 |
| 3,780,027 | 12/1973 | Cragoe, Jr. et al. | 564/162 |
| 4,178,387 | 12/1979 | Diamond et al. | 424/322 |
| 4,251,545 | 2/1981 | Resnick | 424/327 |
| 5,091,394 | 2/1992 | Englert et al. | 514/331 |
| 5,373,024 | 12/1994 | Lang et al. | 514/618 |

FOREIGN PATENT DOCUMENTS 0 416 499 A2  3/1991  European Pat. Off. ................ 514/331

OTHER PUBLICATIONS

Chemical Abstracts, vol. 54, No. 1, Abstract No. 3198e, Jan. 10, 1960.

"Na$^+$/H$^+$ Exchange in Porcine Cerebral Capillary . . . ", Biochemical and Biophysical Research Communications, Schmid et al., 184(1):112–117 (1992).

European Patent Office Search Report, 1993.

A. Buschauer, "Synthesis and in Vitro Pharmacology of Arpromidine and Related Phenyl(pyridylalkyl) quanidines, a Potential New Class of Positive Inotropic Drugs," J. Med. Chem. 32:1963–1970 (1989).

"Antiarrhythmic and Electrophysiologic Actions in Patients With Inducible Sustained Ventricular Tachycardia", Henry J. Duff et. al., Circulation, 79(6):1257–1263 (1989).

*Primary Examiner*—Zinna Northington Davis
*Attorney, Agent, or Firm*—Finnegan, Henderson, Farabow, Garrett & Dunner, L.L.P.

[57] ABSTRACT

3,4,5-Substituted benzoylguanidines, process for their preparation, their use as a medicament or diagnostic and medicament containing them Benzoylguanidines of the formula I

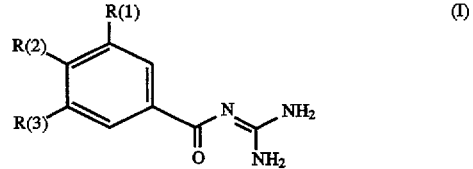

where R(1) is R(4)—SO$_m$ or R(5)R(6)N—SO$_2$—, where R(4) and R(5) are alk(en)yl, —C$_n$H$_{2n}$—R(7), and where R(7) is cycloalkyl or phenyl, where R(5) is also H, R(6) is H or C$_1$—C$_4$—alkyl, R(2) is hydrogen, (cyclo)-alk(en)(yn)yl, aryl and hetaryl, R(3) is defined as R(2)

and their pharmaceutically tolerable salts are described.

12 Claims, No Drawings

3,4,5-SUBSTITUTED BENZOYLGUANIDINES, PROCESS FOR THEIR PREPARATION, THEIR USE AS A MEDICAMENT OR DIAGNOSTIC AND MEDICAMENT CONTAINING THEM

This application is a continuation of prior application Ser. No. 08/303,006 filed Sep. 8, 1994, now abandoned which is a continuation of first-filed application Ser. No. 08/083,576 filed Jun. 30, 1993, now abandoned.

DESCRIPTION 3,4,5-Substituted benzoylguanidines, process for their preparation, their use as a medicament or diagnostic and medicament containing them The invention relates to benzoylguanidines of the formula I

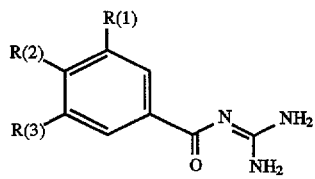

in which:

R(1) is R(4)—$SO_m$ or R(5)R(6)N—$SO_2$—, where m is zero, 1 or 2,

R(4) and R(5) are $C_1$-$C_8$-alkyl, $C_3$-$C_6$-alkenyl or —$C_nH_{2n}$—R(7), n is zero, 1, 2, 3 or 4, R(7) is $C_5$-$C_7$-cycloalkyl, or phenyl which is unsubstituted or substituted by 1–3 substituents from the group comprising F, Cl, $CF_3$, methyl, methoxy and NR(8)R(9) where R(8) and R(9) are H or $C_1$-$C_4$-alkyl, where R(5) is also H, R(6) is H or $C_1$-$C_4$-alkyl, where R(5) and R(6) together can be 4 or 5 methylene groups, of which one $CH_2$ group can be replaced by an O, S, NH, N—$CH_3$ or N-benzyl, R(2) is hydrogen, straight-chain or branched ($C_5$-$C_8$)-alkyl, —CR(13)=CHR(12) or —C≡CR(12) where R(12) is phenyl which is unsubstituted or substituted by 1–3 substituents from the group comprising F, Cl, $CF_3$, methyl, methoxy and NR(14)R(15) where R(14) and R(15) are H or ($C_1$-$C_4$)-alkyl, or R(12) is ($C_1$-$C_9$)-heteroaryl which is unsubstituted or substituted as phenyl, or ($C_1$-$C_6$)-alkyl which is unsubstituted or substituted by 1–3 OH, or ($C_3$-$C_8$) -cycloalkyl;

R(13) is hydrogen or methyl, ($C_3$-$C_8$)-cycloalkyl, ($C_3$-$C_8$)-cycloalkyl-($C_1$-$C_4$)-alkyl, phenyl, $C_6H_5$-($C_1$-$C_4$)-alkyl, naphthyl, biphenylyl, 1,1-diphenyl-($C_1$-$C_4$)-alkyl, cyclopentadienyl, pyridyl, pyrrolyl, furanyl, thienyl, thiazolyl, oxazolyl, indenyl, quinolyl, indolyl, benzofuranyl, benzothienyl, benzothiazolyl, benzoxazolyl, imidazolyl, pyrazolyl, triazolyl, tetrazolyl, isoxazolyl, isothiazolyl, pyrazinyl, pyrimidinyl, pyridazinyl, indazolyl, isoquinolyl, phthalazinyl, quinoxalinyl, quinazolinyl, cinnolinyl, R(3) is defined as R(2), and where the aromatic substituents R(2) or R(3) are unsubstituted or substituted by 1–3 substituents from the group comprising F, Cl, $CF_3$, ($C_1$-$C_4$)-alkyl or -alkoxy, and NR(10)R(11) where R(10) and R(11) are H or ($C_1$-$C_4$)-alkyl, but where R(2) and R(3) cannot simultaneously be hydrogen, and their pharmaceutically tolerable salts.

Preferred compounds I are those in which:

R(1) is R(4)—$SO_m$ or R(5)R(6)N—$SO_2$—, where m is zero, 1 or 2,

R(4) and R(5) are $C_1$-$C_8$-alkyl, $C_3$-$C_4$-alkenyl or —$C_nH_{2n}$—R(7), n is zero or 1, R(7) is $C_5$-$C_6$-cycloalkyl, or phenyl which is unsubstituted or substituted by 1–3 substituents from the group comprising F, Cl, $CF_3$, methyl, methoxy and NR(8)R(9) where R(8) and R(9) are H or methyl, where R(5) is also H, R(6) is H or methyl, where R(5) and R(6) together can be 4 or 5 methylene groups, of which one $CH_2$ group can be replaced by an O, S, N—$CH_3$ or N-benzyl, R(2) is hydrogen, straight-chain or branched ($C_5$-$C_8$)-alkyl, ($C_3$-$C_8$)-cycloalkyl, ($C_3$-$C_8$)-cycloalkyl-($C_1$-$C_2$)-alkyl, phenyl, $C_6H_5$-($C_1$-$C_2$)-alkyl, naphthyl, biphenylyl, pyridyl, pyrrolyl or —C≡CR(12) where R(12) is phenyl which is unsubstituted or substituted by 1–3 substituents from the group comprising F, Cl, $CF_3$, methyl, methoxy or NR(14)R(15) where R(14) and R(15) are H or ($C_1$-$C_4$)-alkyl, or R(12) is ($C_1$-$C_9$)-heteroaryl which is unsubstituted or substituted as phenyl, or ($C_1$-$C_6$)-alkyl which is unsubstituted or substituted by 1–3 OH, or ($C_3$-$C_8$)-cycloalkyl;

R(3) is defined as R(2), and where the aromatic substituents R(2) and R(3) are unsubstituted or substituted by 1–3 substituents from the group comprising F, Cl, $CF_3$, ($C_1$-$C_4$)-alkyl or -alkoxy, and MR(10)R(11) where R(10) and R(11) are H or ($C_1$-$C_4$)-alkyl, but where R(2) and R(3) cannot simultaneously be hydrogen, and their pharmaceutically tolerable salts.

Particularly preferred compounds of the formula I are those in which:

R(1) is R(4)—$SO_m$ or R(5)R(6)N—$SO_2$—, where m is zero, 1 or 2,

R(4) is methyl or —$C_nH_{2n}$—R(7), n is zero or 1,

R(7) is phenyl which is unsubstituted or substituted by 1–3 substituents from the group comprising Cl, $CF_3$, methyl and methoxy, R(5) is H, $C_1$-$C_6$-alkyl, allyl or —$C_nH_{2n}$—R(7), n is zero, 1, R(7) is phenyl which is unsubstituted or substituted by 1–3 substituents from the group comprising F, Cl, $CF_3$, methyl, methoxy or NR(8)R(9) where R(8) and R(9) are H or methyl, R(6) is H or methyl, where R(5) and R(6) can together be 4 or 5 methylene groups, of which one CH2 group can be replaced by an O, S, N—CH$_3$ or N-benzyl, R(2) is hydrogen, straight-chain or branched ($C_5$–$C_8$)-alkyl, ($C_3$–$C_8$)-cycloalkyl, ($C_3$–$C_8$)-cycloalkyl-($C_1$–$C_2$)-alkyl, phenyl, $C_6H_5$-($C_1$–$C_2$)-alkyl, naphthyl, biphenylyl, pyridyl, pyrrolyl or —C≡CR(12) where R(12) is phenyl which is unsubstituted or substituted by 1–3 substituents from the group comprising F, Cl, CF$_3$, methyl, methoxy and NR(14)R(15) where R(14) and R(15) are H or ($C_1$–$C_4$)-alkyl, or R(12) is ($C_1$–$C_9$)-heteroaryl which is unsubstituted or substituted as phenyl, or ($C_1$–$C_6$)-alkyl which is unsubstituted or substituted by 1–3 OH, or ($C_3$–$C_8$)-cycloalkyl;

R(3) is hydrogen, phenyl, cyclopentyl, $C_6H_5$-($C_1$–$C_2$)-alkyl, or —C≡CR(12) where R(12) is phenyl which is unsubstituted or substituted by 1–3 substituents from the group comprising F, Cl, CF$_3$, methyl, methoxy and NR(14)R(15) where R(14) and R(15) are H or ($C_1$–$C_4$)-alkyl, or R(12) is ($C_1$–$C_9$)-heteroaryl which is unsubstituted or substituted as phenyl, or ($C_1$–$C_6$)-alkyl which is unsubstituted or substituted by 1–3 OH, or ($C_3$–$C_8$)-cycloalkyl;

where the aromatic substituents R(2) and R(3) are unsubstituted or substituted by 1–3 substituents from the group comprising F, Cl, CF$_3$, ($C_1$–$C_4$)-alkyl or -alkoxy, and NR(10)R(11) where R(10) and R(11) are H or ($C_1$–$C_4$)-alkyl, and where, however, R(2) and R(3) cannot simultaneously be hydrogen, and their pharmaceutically tolerable salts.

If one of the substituents R(1) to R(15) contains a center of asymmetry, the invention includes compounds having both the S and R configurations. The compounds can be present as optical isomers, as diastereomers, as racemates or as mixtures thereof.

If not expressly mentioned otherwise, the alkyl radicals can be either straight-chain or branched.

The invention furthermore relates to a process for the preparation of the compounds I, which comprises reacting compounds of the formula II

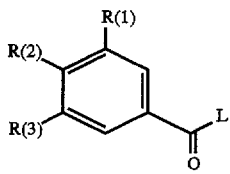

(II)

with guanidine, in which R(1) to R(3) have the given meaning and L is a leaving group which can be easily nucleophilically substituted.

The activated acid derivatives of the formula II in which L is an alkoxy group, preferably a methoxy group, a phenoxy group, or phenylthio, methylthio or 2-pyridylthio group, or a nitrogen heterocycle, preferably 1-imidazolyl, are advantageously obtained in a manner known per se from the carbonyl chlorides (formula II, L=Cl) on which they are based, which for their part can in turn be prepared in a manner known per se from the carboxylic acids (formula II, L=OH) on which they are based, for example using thionyl chloride.

In addition to the carbonyl chlorides of the formula II (L=Cl), other activated acid derivatives of the formula II can also be prepared in a manner known per se directly from the benzoic acid derivatives (formula II, L=OK) on which they are based, such as, for example, the methyl esters of the formula II where L=OCH$_3$ by treatment with gaseous HCl in methanol, the imidazolides of the formula II by treatment with carbonyldiimidazole (L=1-imidazolyl, Staab, Angew. Chem. Int. Ed. Engl. 1, 351–367 (1962)), the mixed anhydrides II using Cl—COOC$_2$H$_5$ or tosyl chloride in the presence of triethylamine in an inert solvent, and also the activation of benzoic acids using dicyclohexylcarbodiimide (DCC) or using O-[(cyano(ethoxycarbonyl)methylene)amino]-1,1,3,3-tetramethyluronium tetrafluoborate ("TOTU") (Weiss and Krommer, Chemiker Zeitung 98, 817 (1974)). A number of suitable methods for the preparation of activated carboxylic acid derivatives of the formula II are given under details of source literature in J. March, Advanced Organic Chemistry, Third Edition (John Wiley & Sons, 1985), p. 350.

The reaction of an activated carboxylic acid derivative of the formula II with guanidine is carried out in a manner known per se in a protic or aprotic polar but inert organic solvent. Methanol or THF between 20° C. and the boiling point of these solvents have proven suitable in the reaction of the methyl benzoates (II, L=OMe) with guanidine. In most reactions of compounds II with salt-free guanidine, the reaction was advantageously carried out in aprotic inert solvents such as THF, dimethoxyethane or dioxane. However, water can also be used as a solvent in the reaction of II and guanidine using a base such as, for example, NaOH.

If L=Cl, the reaction is advantageously carried out with the addition of an acid scavenger, for example in the form of excess guanidine, for binding the hydrohalic acid.

Some of the underlying benzoic acid derivatives of the formula II are known and described in the literature. The unknown compounds of the formula II can be prepared by methods known from the literature by converting, for example, 4- (or 5-)halo-3-chlorosulfonylbenzoic acids with ammonia or amines into 3-aminosulfonyl-4-(or 5-)halobenzoic acids or with a weak reductant such as sodium bisulfite and subsequent alkylation into 3-alkylsulfonyl-4-(or 5-)halobenzoic acids and reacting the resulting benzoic acids according to one of the process variants described above to give compounds I according to the invention.

The introduction of the substituents in the 4- and 5-position is carried out by methods known from the literature for the palladium-mediated cross-coupling of aryl halides with, for example, organozinc or organo-copper compounds, organostannanes, organoboronic acids or organoboranes.

In general, benzoylguanidines I are weak bases and can bind acid with the formation of salts. Possible acid addition salts are salts of all pharmacologically tolerable acids, for example halides, in particular hydrochlorides, lactates, sulfates, titrates, tartrates, acetates, phosphates, methanesulfonates and p-toluene-sulfonates.

The compounds I are substituted acylguanidines. The most prominent representative of the acylguanidines is the pyrazine derivative amiloride, which is used in therapy as a potassium-sparing diuretic. Numerous other compounds of the amiloride type are described in the literature, such as, for example, dimethylamiloride or ethylisopropylamiloride.

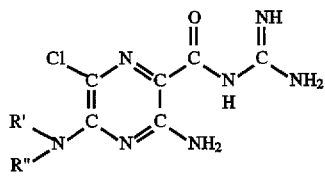

Amiloride: R', R"=H

Dimethylamiloride: R', R"=CH$_3$

Ethylisopropylamiloride: R'=C$_2$H$_5$, R"=CH(CH$_3$)$_2$

Investigations have moreover been disclosed which point to antiarrhythmic properties of amiloride (Circulation 79, 1257–63 (1989). Obstacles to wide use as an anti-arrhythmic are, however, the fact that this effect is only slightly pronounced and occurs accompanied by a hypotensive and saluretic action and these side effects are undesired in the treatment of cardiac arrhythmias.

Indications of antiarrhythmic properties of amiloride were also obtained in experiments on isolated animal hearts (Eur. Heart J. 9 (suppl.1): 167 (1988) (book of abstracts)). For instance, it was found in rat hearts that an artificially induced ventricular fibrillation could be suppressed completely by amiloride. The above-mentioned amiloride derivative ethylisopropylamiloride was even more potent than amiloride in this model.

U.S. Pat. No. 5,091,394 (HOE 89/F 288) describes benzoylguanidines which carry a hydrogen atom in the position corresponding to the radical R(3). German Patent Application P 42 04 575.4 (HOE 92/F 034) proposes 3,5-substituted benzoylguanidines in which, however, the substituents R(2) and R(3) do not have the meaning claimed according to the present invention.

In U.S. Pat. No. 3,780,027, acylguanidines are claimed which are structurally similar to the compounds of the formula I and are derived from commercially available loop diuretics, such as bumetanide. A strong salidiuretic activity is correspondingly reported for these compounds.

It was therefore surprising that the compounds according to the invention have no undesired and disadvantageous salidiuretic properties, but very good antiarrhythmic properties, as occur, for example, in the case of oxygen deficiency symptoms. As a result of their pharmacological properties, the compounds are outstandingly suitable as antiarrhythmic pharmaceuticals having a cardioprotective component for infarct prophylaxis and infarct treatment and for the treatment of angina pectoris, where they also preventively inhibit or greatly decrease the patho-physiological processes in the formation of ischemically induced damage, in particular in the production of ischemically induced cardiac arrhythmias. Because of their protective actions against pathological hypoxic and ischemic situations, the compounds of the formula I according to the invention can be used as a result of inhibition of the cellular Na$^+$/H$^+$ exchange mechanism as pharmaceuticals for the treatment of all acute or chronic damage caused by ischemia or primary or secondary diseases induced thereby. This relates to their use as pharmaceuticals for surgical interventions, for example in organ transplantations, where the compounds can be used both for the protection of the organs in the donor before and during removal, for the protection of removed organs, for example during treatment with or storage thereof in physiological bath fluids, and during transfer to the body of the recipient. The compounds are also useful protective pharmaceuticals during the performance of angioplastic surgical interventions, for example in the heart and in peripheral vessels. In accordance with their protective action against ischemically induced damage, the compounds are also suitable as pharmaceuticals for the treatment of ischemias of the nervous system, in particular the central nervous system, where they are suitable, for example, for the treatment of stroke or of cerebral edema. Moreover, the compounds of the formula I according to the invention are also suitable for the treatment of forms of shock, such as, for example, allergic, cardiogenic, hypovolemic and bacterial shock.

Moreover, the compounds of the formula I according to the invention are distinguished by potent inhibitory action on the proliferation of cells, for example fibroblast cell proliferation and the proliferation of vascular smooth muscle cells. The compounds of the formula I can therefore be considered as useful therapeutics for diseases in which cell proliferation is a primary or secondary cause, and can therefore be used as antiatherosclerotics, agents against diabetic late complications, cancers, fibrotic diseases such as pulmonary fibrosis, fibrosis of the liver or fibrosis of the kidneys, organ hypertrophy and hyperplasia, in particular in prostate hyperplasia or prostate hypertrophy.

The compounds according to the invention are active inhibitors of the cellular sodium-proton antiporter (Na$^+$/H$^+$ exchanger), which is raised in numerous diseases (essential hypertension, atherosclerosis, diabetes, etc.) even in those cells which are easily accessible to measurements, such as, for example, in erythrocytes, thrombocytes or leucocytes. The compounds according to the invention are therefore suitable as excellent and simple scientific tools, for example in their use as diagnostics for the determination and differentiation of certain forms of hypertension, but also of atherosclerosis, of diabetes, proliferative diseases etc. Moreover, the compounds of the formula I are suitable for preventive therapy for the prevention of the formation of high blood pressure, for example of essential hypertension.

Pharmaceuticals which contain a compound I can be administered orally, parenterally, intravenously, rectally or by inhalation, the preferred administration being dependent on the particular type of the disease. The compounds I can be used on their own or together with pharmaceutical auxiliaries, to be precise in veterinary and in human medicine.

The auxiliaries which are suitable for the desired pharmaceutical formulation are familiar to the person skilled in the art on the basis of his expert knowledge. In addition to solvents, gelling agents, suppository bases, tabletting auxiliaries and other active compound excipients, it is possible to use, for example, antioxidants, dispersants, emulsifiers, antifoams, flavor correctants, preservatives, solubilizers or colorants.

For a form for oral administration, the active compounds are mixed with the additives suitable for this purpose, such as excipients, stabilizers or inert diluents, and are brought by the customary methods into the suitable administration forms, such as tablets, coated tablets, hard gelatine capsules, or aqueous, alcoholic or oily solutions. Inert excipients which can be used are, for example, gum arabic, magnesia, magnesium carbonate, potassium phosphate, lactose, glucose or starch, in particular corn starch. Preparation can be carried out here both as dry and as moist granules. Suitable oily excipients or solvents are, for example, vegetable or animal oils, such as sunflower oil or fish liver oil.

For subcutaneous or intravenous administration, the active compounds are brought into solution, suspension or emulsion, if desired using the substances customary for this purpose such as solubilizers, emulsifiers or other auxiliaries. Suitable solvents are, for example: water, physiological saline solution or alcohols, for example ethanol, propanol, glycerol, and also sugar solutions such as glucose or mannitol solutions, or alternatively a mixture of the various solvents mentioned.

Pharmaceutical formulations suitable for administration in the form of aerosols or sprays are, for example, solutions, suspensions or emulsions of the active compound of the formula I in a pharmaceutically acceptable solvent, such as, in particular, ethanol or water, or a mixture of these solvents.

If required, the formulation can also contain still other pharmaceutical auxiliaries such as surfactants, emulsifiers and stabilizers as well as a propellant gas. Such a preparation contains the active compound customarily in a concentration from about 0.1 to 10, in particular from about 0.3 to 3% by weight.

The dose of the active compound of the formula I to be administered and the frequency of administration depend on the potency and duration of action of the compounds used and additionally on the type and severity of the disease to be treated and on the sex, age, weight and individual responsiveness of the mammal to be treated. On average, the daily dose of a compound of the formula I in a patient weighing about 75 kg is at least 0.001 mg/kg, preferably 0.01 mg/kg to 10 mg/kg, preferably 1 mg/kg of body weight. In acute episodes of the disease, for example immediately after suffering a cardiac infarct, even higher and in particular more frequent dosages may be necessary, for example up to 4 individual doses per day. In particular when administered i.v., for example in the case of an infarct patient in the intensive care unit, up to 200 mg per day may be necessary.

Experimental Section

General procedure for the preparation of benzoylguanidines (I) from benzoic acids (II, L=OH)

0.01 mol of the benzoic acid derivative of the formula II is dissolved or suspended in 60 ml of anhydrous tetrahydrofuran (THF) and then treated with 1.78 g (0.011 mol) of carbonyldiimidazole. After stirring for 2 hours at room temperature, 2.95 g (0.05 mol) of guanidine are introduced into the reaction solution. After stirring overnight, the THF is distilled off under reduced pressure (Rotavapor), the residue is treated with water, the mixture is adjusted to pH 6–7 with 2N HCl and the corresponding benzoylguanidine (formula I) is filtered off. The benzoylguanidines obtained in this way can be converted into the corresponding salts by treatment with aqueous or methanolic hydrochloric acid or other pharmacologically tolerable acids.

EXAMPLE 1

3-Methylsulfonyl-4-phenylbenzoylguanidine hydrochloride: colorless crystals, m.p. 196°–98° C.
Synthetic route:
a) Reduction of 4-bromo-3-chlorosulfonylbenzoic acid to 2-bromo-5-carboxybenzenesulfinic acid using sodium disulfite in water at 10°–15° C. and constant pH (8–9), acidify with HCl and filter off the precipitate, m.p. 220°–22° C.
b) Disodium 2-bromo-5-carboxybenzenesulfinate from a) using 2 equivalents of NaOH in water/methanol, evaporate, suspend in acetone and filter off crystals, m.p.>300° C.
c) React methyl 4-bromo-3-methylsulfonylbenzoate from b) with 3.5 equivalents of methyl iodide in DMF at 80° C./6 h, remove solvent by distillation, suspend residue in water, filter off crystals with suction, m.p. 135°–37° C.
d) 3-Methylsulfonyl-4-phenylbenzoic acid from c) using 1.1 equivalents of phenylboronic acid in an aqueous methanol/toluene mixture (reflux, 3 h) in the presence of catalytic palladium acetate, triphenylphosphine and sodium carbonate, remove solvent by distillation, take up in ethyl acetate, render neutral with dil. hydrochloric acid, after aqueous work up, column chromatography on silica gel using ethyl acetate/cyclohexane (3:7).
e) 3-Methylsulfonyl-4-phenylbenzoylguanidine hydrochloride from d) according to general procedure I (see above). Colorless crystals, m.p. 196°–98° C.

EXAMPLE 2

3-Methylsulfonyl-4-(2-naphthyl)benzoylguanidine hydrochloride: colorless powder, amorphous.
Synthetic route:
a) Methyl 3-methylsulfonyl-4-(2-naphthyl)benzoate from methyl 4-bromo-3-methylsulfonylbenzoate by cross-coupling with 2-naphthylboronic acid analogously to Example 1d), colorless powder, amorphous.
b) 3-Methylsulfonyl-4-(2-naphthyl)benzoylguanidine hydrochloride from 2a) by heating to boiling in THF in the presence of guanidine and subsequent hydrochloride formation, colorless powder, amorphous.

EXAMPLE 3

3-Methylsulfonyl-4-(3-biphenyl)benzoylguanidine hydrochloride: sand-colored crystals, m.p. 150°–54° C.
Synthetic route:
a) Methyl 3-methylsulfonyl-4-(3-biphenyl)benzoate from methyl 4-bromo-3-methylsulfonylbenzoate by cross-coupling with 3-biphenylboronic acid analogously to 1d), slightly yellowish crystals, m.p. 77°–80° C.
b) 3-Methylsulfonyl-4-(3-biphenyl)benzoylguanidine hydrochloride from 3a) by heating to boiling in THF in the presence of guanidine and subsequent hydrochloride formation.

EXAMPLE 4

4-Cyclopropyl-3-methylsulfonylbenzoylguanidine hydrochloride: colorless crystals, m.p. 233°–35° C.
Synthetic route:
a) Methyl 4-cyclopropyl-3-methylsulfonylbenzoate from methyl 4-bromo-3-methylsulfonylbenzoate (1c) using 1.5 equivalents of cyclopropyl-tri-n-butylstannane in hexamethylphosphoramide (65° C., 6 h) in the presence of catalytic palladium(II) [1,1'-bis(diphenylphosphino) ferrocene] chloride and copper(I) iodide, aqueous work-up, extraction with ethyl acetate and subsequent column chromatography on silica gel using ethyl acetate/cyclohexane (3:7), m.p. 81°–83° C.
b) 4-Cyclopropyl-3-methyl sulfonylbenzoylguanidine hydrochloride from 4a) analogously to Example 2b), m.p. 233°–35° C.

EXAMPLE 5

4-Cyclohexyl-3-methylsulfonylbenzoylguanidine hydrochloride: colorless crystals, m.p. 230°–32° C.
Synthetic route:
a) Methyl 4-cyclohexyl-3-methylsulfonylbenzoate analogously to Example 1a–c) starting from 4-cyclohexyl-3-chlorosulfonylbenzoic acid, m.p. 91°–93° C.

b) 4-Cyclohexyl-3-methylsulfonylbenzoylguanidine hydrochloride analogously to Example 2b), m.p. 230°–32° C.

EXAMPLE 6

3-Methylsulfonyl-4-(2'-pyridyl)benzoylguanidine hydrochloride: colorless crystals, m.p. 249°–50° C.
Synthetic route:
  a) Methyl 3-methylsulfonyl-4-(2'-pyridyl)benzoate from methyl 4-bromo-3-methylsulfonylbenzoate (1c) using 1.5 equivalents of 2-pyridyl-tri-n-butylstannane in THF (boiling heat, 18 h) in the presence of catalytic palladium(II) [1,1'-bis(diphenylphosphino)ferrocene] chloride and copper(I) iodide, aqueous work-up, extraction with ethyl acetate and subsequent column chromatography on silica gel using ethyl acetate/cyclohexane (1:1), m.p. 152°–155° C.
  b) 3-Methylsulfonyl-4-(2'-pyridyl)benzoylguanidine hydrochloride from 6a) analogously to Example 2b).

EXAMPLE 7

3-Methylsulfonyl-4-[(2'-phenyl)ethynyl]benzoylguanidine hydrochloride: colorless crystals, m.p. 287° C.
Synthetic route:
  a) Methyl 3-methylsulfonyl-4-[(2'-phenyl)ethynyl]-benzoate from methyl 4-bromo-3-methylsulfonylbenzoate (1c) by Stephans-Castro coupling with 2.5 equivalents of phenylacetylene, stirring at room temperature for 24 h in the presence of catalytic (5 mol %) bis(triphenylphosphine)palladium(II) chloride, 15 mol % of copper(I) iodide and 3 equivalents of n-butylamine, aqueous ammonium chloride work-up, extraction with ethyl acetate and subsequent column chromatography on silica gel using ethyl acetate/cyclohexane (3:7), colorless crystals, m.p. 138°–39° C.
  b) 3-Methylsulfonyl-4-[(2'-phenyl)ethynyl]benzoylguanidine hydrochloride from 7a) analogously to Example 2b).

EXAMPLE 8

4-[(2'-Cyclohexyl)ethynyl]-3-methylsulfonylbenzoylguanidine hydrochloride: colorless crystals, m.p. 224°–25° C.
Synthetic route:
  a) Methyl 4-[(2'-cyclohexyl)ethynyl]-3-methylsulfonylbenzoate from methyl 4-bromo-3-methylsulfonylbenzoate (1c) by Stephans-Castro coupling as described for 7a), coupling component cyclohexylacetylene, colorless crystals, m.p. 81°–82° C.
  b) 4-[(2'-Cyclohexyl)ethynyl]-3-methylsulfonylbenzoylguanidine hydrochloride from 8a) analogously to Example 2b).

EXAMPLE 9

3-Methylsulfonyl-4-phenylethylbenzoylguanidine hydrochloride: colorless crystals, m.p. 230°–31° C.
Synthetic route:
  a) Methyl 3-methylsulfonyl-4-phenylethylbenzoate from 7a) by palladium/carbon hydrogenation under normal pressure in methanol for 1 h, colorless crystals, m.p. 91°–93° C.
  b) 3-Methylsulfonyl-4-phenylethylbenzoylguanidine hydrochloride from 9a) analogously to Example 2b).

EXAMPLE 10

4-Cyclopentyl-3-methylsulfonylbenzoylguanidine hydrochloride: colorless crystals, m.p. 243°–45° C.
Synthetic route:
  a) Methyl 4-cyclopentyl-3-methylsulfonylbenzoate from methyl 4-bromo-3-methylsulfonylbenzoate (1c) by cross-coupling with 1.5 equivalents of cyclopentylzinc chloride (from cyclopentylmagnesiumchloride by transmetalation with zinc(II) chloride etherate in THF) by stirring at room temperature in the presence of catalytic palladium(II) [1,1'-bis(diphenylphosphino)ferrocene] chloride and copper(I) iodide, aqueous work-up, extraction with ethyl acetate and subsequent column chromatography on silica gel using ethyl acetate/n-heptane (3:7), colorless crystals, m.p. 143°–44° C.
  b) 4-Cyclopentyl-3-methylsulfonylbenzoylguanidine hydrochloride from 10a) analogously to Example 2b).

EXAMPLE 11

4-Benzyl-3-methylsulfonylbenzoylguanidine hydrochloride: colorless crystals, m.p. 284° C.
Synthetic route:
  a) Methyl 4-benzyl-3-methylsulfonylbenzoate from methyl 4-bromo-3-methylsulfonylbenzoate (1c) by cross-coupling with 1.5 equivalents of benzylzinc chloride (from benzylmagnesium chloride by transmetalation with zinc(II) chloride etherate in THF), heating to boiling for 2 h in the presence of catalytic (5 mol %) palladium(II) acetate and triphenylphosphine, aqueous work-up, extraction with ethyl acetate and subsequent column chromatography on silica gel using ethyl acetate/cyclohexane (3:7), colorless crystals, m.p. 104°–106° C.
  b) 4-Benzyl-3-methylsulfonylbenzoylguanidine hydrochloride from 11a) analogously to Example 2b).

EXAMPLE 12

3-Methylsulfonyl-5-phenylbenzoylguanidine hydrochloride: colorless crystals, m.p. 230° C.
Synthetic route:
  a) Methyl 3-methylsulfonyl-5-phenylbenzoate from methyl 3-bromo-5-methylsulfonylbenzoate by cross-coupling with phenylboronic acid analogously to Example 1d), colorless powder, m.p. 126°–28° C.
  b) 3-Methylsulfonyl-5-phenylbenzoylguanidine hydrochloride from 12a) by heating to boiling in THF in the presence of guanidine and subsequent hydrochloride formation.

EXAMPLE 13

3-Cyclopentyl-5-methylsulfonylbenzoylguanidine hydrochloride: colorless crystals, m.p. 204°–206° C.
Synthetic route:
  a) Methyl 3-cyclopentyl-5-methylsulfonylbenzoate from methyl 3-bromo-5-methylsulfonylbenzoate by cross-coupling with cyclopentylzinc chloride analogously to Example 10a), colorless crystals, m.p. 85° C.
  b) 3-Cyclopentyl-5-methylsulfonylbenzoylguanidine hydrochloride from 13a) analogously to Example 12b).

Pharmacological data:
Inhibitors of the $Na^+/H^+$ exchanger of rabbit erythrocytes:
White New Zealand rabbits (Ivanovas) received a standard diet containing 2% cholesterol for six weeks in order to activate Na⁺/H⁺ exchange and thus to be able to determine the Na⁺ influx into the erythrocytes via Na⁺/H⁺ exchange by flame photometry. The blood was taken from the ear arteries and rendered incoagulable by 25 IU/ml of potassium heparin. A part of each sample was used for the duplicate determination of the hematocrit by centrifugation. Aliquots of 100 µl in each case were used to measure the Na⁺ starting content of the erythrocytes.

In order to determine the amiloride-sensitive sodium influx, 100 µl of each blood sample were incubated at pH 7.4 and 37° C. in 5 ml in each case of a hyperosmolar salt/sucrose medium (mmol/l:140 NaCl, 3 KCl, 150 sucrose, 0.1 ouabain, 20 tris(hydroxymethyl)aminomethane). The erythrocytes were then washed three times with ice-cold $MgCl_2$/ouabain solution (mmol/l:112 $MgCl_2$, 0.1 ouabain) and hemolized in 2.0 ml of distilled water. The intracellular sodium content was determined by flame photometry.

The Na⁺ net influx was calculated from the difference between sodium starting values and the sodium content of the erythrocytes after incubation. The amiloride-inhibitable sodium influx resulted from the difference between the sodium content of the erythrocytes after incubation with and without $3 \times 10^{-4}$ mol/l amiloride. The process was also carried out in this manner in the case of the compounds according to the invention.

Results

Inhibition of the Na⁺/H⁺ exchanger:

| Example | $IC_{50}$ (mol/l) |
| --- | --- |
| 1 | $2 - 3 \times 10^{-6}$ |
| 2 | $5 \times 10^{-7}$ |
| 3 | greater than $10^{-6}$ |
| 4 | $3 - 5 \times 10^{-6}$ |
| 5 | $1.7 \times 10^{-6}$ |
| 6 | greater than $10^{-6}$ |
| 7 | $2 \times 10^{-7}$ |
| 8 | $3 - 9 \times 10^{-6}$ |
| 9 | $9 \times 10^{-7}$ |
| 10 | $1 \times 10^{-7}$ |
| 11 | $5 - 7 \times 10^{-6}$ |
| 12 | $3 - 5 \times 10^{-6}$ |
| 13 | $3 \times 10^{-6}$ |

We claim:

1. A benzoylguanidine of the formula I

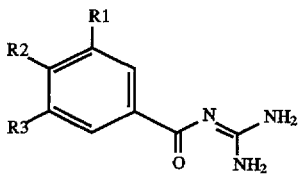

in which

R(1) is R(4)—$SO_m$— or R(5)R(6)N—$SO_2$—;

m is zero, 1 or 2;

R(4) and R(5) are $C_1$–$C_8$-alkyl, $C_3$–$C_6$-alkenyl or —$C_nH_{2n}$—R(7);

n is zero, 1, 2, 3 or 4;

R(7) is $C_5$–$C_7$-cycloalkyl or phenyl, which is unsubstituted or substituted by 1–3 substituents selected from the group consisting of F, Cl, $CF_3$, methyl, methoxy and NR(8)R(9);

R(8) and R(9) are H or $C_1$–$C_4$-alkyl;

where

R(5) is also H;

R(6) is H or $C_1$–$C_4$-alkyl;

or

R(5) and R(6) together are 4 or 5 methylene groups, of which one $CH_2$ group can be replaced by an O, S, NH, N—$CH_3$ or N-benzyl;

R(2) is hydrogen, straight or branched ($C_5$–$C_8$)-alkyl, —CR(13)=CHR(12) or —C≡CR(12);

R(12) is cycloalkyl or phenyl, which is unsubstituted or substituted by 1–3 substituents selected from the group consisting of F, Cl, $CF_3$, methyl, methoxy and NR(14)R(15);

R(14) and R(15) are H or ($C_1$–$C_4$)-alkyl;

R(13) is hydrogen or methyl;

or

R(2) is ($C_3$–$C_8$)-cycloalkyl, ($C_3$–$C_8$)-cycloalkyl-($C_1$–$C_4$)-alkyl, phenyl, $C_6H_5$-($C_1$–$C_4$)-alkyl, naphthyl, biphenyl, 1,1-diphenyl-($C_1$–$C_4$)-alkyl or cyclopentadienyl;

R(3) is defined as R(2);

and where the aromatic substituents phenyl, naphthyl, biphenylyl and diphenylyl of R(2) and R(3) are unsubstituted or substituted by 1–3 substituents selected from the group consisting of F, Cl, $CF_3$, ($C_1$–$C_4$)-alkyl or -alkoxy, and NR(10)R(11);

R(10) and R(11) are H or ($C_1$–$C_4$)-alkyl;

but where R(2) and R(3) cannot simultaneously be hydrogen, or a pharmaceutically tolerable salt thereof.

2. A compound as claimed in claim 1, wherein:

R(1) is R(4)—$SO_m$ or R(5)R(6)N—$SO_2$—, where m is zero, 1 or 2,

R(4) and R(5) are $C_1$–$C_8$-alkyl, $C_3$–$C_4$-alkenyl or —$C_nH_{2n}$—R(7), n is zero or 1, R(7) is $C_5$–$C_6$-cycloalkyl, or phenyl which is unsubstituted or substituted by 1–3 substituents from the group comprising F, Cl, $CF_3$, methyl, methoxy and NR(8)R(9) where R(8) and R(9) are H or methyl, where R(5) is also H, R(6) is H or methyl, where R(5) and R(6) together can be 4 or 5 methylene groups, of which one $CH_2$ group can be replaced by an O, S, N—$CH_3$ or N-benzyl, R(2) is hydrogen, straight-chain or branched ($C_5$–$C_8$)-alkyl, ($C_3$–$C_8$)-cycloalkyl, ($C_3$–$C_8$)-cycloalkyl-($C_1$–$C_2$)-alkyl, phenyl, $C_6H_5$-($C_1$–$C_2$)-alkyl, naphthyl, biphenylyl, pyridyl, pyrrolyl or —C≡CR(12) where R(12) is phenyl which is unsubstituted or substituted by 1–3 substituents from the group comprising F, Cl, $CF_3$, methyl, methoxy and NR(14)R(15) where R(14) and R(15) are H or ($C_1$–$C_4$)-alkyl, or R(12) is ($C_1$–$C_9$)-heteroaryl which is unsubstituted or substituted as phenyl, or ($C_1$–$C_6$)-alkyl which is unsubstituted or substituted by 1–3 OH, or ($C_3$–$C_8$)-cycloalkyl;

R(3) is defined as R(2), where the aromatic substituents R(2) and R(3) are unsubstituted or substituted by 1–3 substituents from the group comprising F, Cl, $CF_3$, ($C_1$–$C_4$)-alkyl or -alkoxy, and NR(10)R(11) where R(10) and R(11) are H or ($C_1$–$C_4$)-alkyl, but where R(2) and R(3) cannot simultaneously be hydrogen, or its pharmaceutically tolerable salts.

3. A compound as claimed in claim 1, wherein:

R(1) is R(4)—SO$_m$ or R(5)R(6)N—SO$_2$—, where m is zero, 1 or 2,

R(4) is methyl or —C$_n$H$_{2n}$—R(7), n is zero or 1,

R(7) is phenyl which is unsubstituted or substituted by 1–3 substituents from the group comprising Cl, CF$_3$, methyl and methoxy, R(5) is H, C$_1$–C$_6$-alkyl, allyl or —C$_n$H$_{2n}$—R(7), n is zero, 1, R(7) is phenyl which is unsubstituted or substituted by 1–3 substituents from the group comprising F, Cl, CF$_3$, methyl, methoxy or NR(8)R(9) where R(8) and R(9) are H or methyl, R(6) is H or methyl, where R(5) and R(6) can together be 4 or 5 methylene groups, of which one CH$_2$ group can be replaced by an O, S, N—CH$_3$ or N-benzyl, R(2) is hydrogen, straight-chain or branched (C$_5$–C$_8$)-alkyl, (C$_3$–C$_8$)-cycloalkyl, (C$_3$–C$_8$)-cycloalkyl-(C$_1$–C$_2$)-alkyl, phenyl, C$_6$H$_5$-(C$_1$–C$_2$)-alkyl, naphthyl, biphenylyl, pyridyl, pyrrolyl or —C≡CR(12) where R(12) is phenyl which is unsubstituted or substituted by 1–3 substituents from the group comprising F, Cl, CF$_3$, methyl, methoxy and NR(14)R(15) where R(14) and R(15) are H or (C$_1$–C$_4$)-alkyl, or R(12) is (C$_1$–C$_9$)-heteroaryl which is unsubstituted or substituted as phenyl, or (C$_1$–C$_6$)-alkyl which is unsubstituted or substituted by 1–3 OH, or (C$_3$–C$_8$)-cycloalkyl;

R(3) is hydrogen, phenyl, cyclopentyl, C$_6$H$_5$-(C$_1$–C$_2$)-alkyl, or —C≡CR(12) where R(12) is phenyl which is unsubstituted or substituted by 1–3 substituents from the group comprising F, Cl, CF$_3$, methyl, methoxy and NR(14)R(15) where R(14) and R(15) are H or (C$_1$–C$_4$)-alkyl, or R(12) is (C$_1$–C$_9$)-heteroaryl which is unsubstituted or substituted as phenyl, or (C$_1$–C$_6$)-alkyl which is unsubstituted or substituted by 1–3 OH, or (C$_3$–C$_8$)-cycloalkyl:

where the aromatic substituents R(2) and R(3) are unsubstituted or substituted by 1–3 substituents from the group comprising F, Cl, CF$_3$, (C$_1$14 C$_4$)-alkyl or -alkoxy, and NR(10)R(11) where R(10) and R(11) are H or (C$_1$–C$_4$)-alkyl, and where, however, R(2) and R(3) cannot simultaneously be hydrogen, or its pharmaceutically tolerable salts.

4. A process for preparing a compound of formula I as claimed in claim 1, which comprises reacting a compound of formula II:

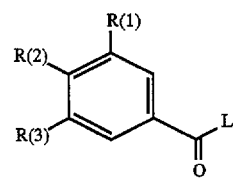

with guanidine, in which

R(1) is R(4)—SO$_m$— or R(5)R(6)N—SO$_2$—;

m is zero, 1 or 2;

R(4) and R(5) are C$_1$–C$_8$-alkyl, C$_3$–C$_6$-alkenyl or —C$_n$H$_{2n}$—R(7);

n is zero, 1, 2, 3 or 4;

R(7) is C$_5$–C$_7$-cycloalkyl or phenyl, which is unsubstituted or substituted by 1–3 substituents selected from the group consisting of F, Cl, CF$_3$, methyl, methoxy and NR(8)R(9);

R(8) and R(9) are H or C$_1$–C$_4$-alkyl;

where

R(5) is also H;

R(6) is H or C$_1$–C$_4$-alkyl:

or

R(5) and R(6) together are 4 or 5 methylene groups, of which one CH$_2$ group can be replaced by an O, S, NH, N—CH$_3$ or N-benzyl;

R(2) is hydrogen, straight or branched (C$_5$–C$_8$)-alkyl, —CR(13)=CHR(12) or —C≡CR(12);

R(12) is cycloalkyl or phenyl, which is unsubstituted or substituted by 1–3 substituents selected from the group consisting of F, Cl, CF$_3$, methyl, methoxy and NR(14)R(15);

R(14) and R(15) are H or (C$_1$–C$_4$)-alkyl:

R(13) is hydrogen or methyl;

or

R(2) is (C$_3$–C$_8$)-cycloalkyl, (C$_3$–C$_8$)-cycloalkyl-(C$_1$–C$_4$)-alkyl, phenyl, C$_6$H$_5$-(C$_1$–C$_4$)-alkyl, naphthyl, biphenyl, 1,1-diphenyl-(C$_1$–C$_4$)-alkyl or cyclopentadienyl;

R(3) is defined as R(2);

and where the aromatic substituents phenyl, naphthyl, biphenylyl and diphenylyl of R(2) and R(3) are unsubstituted or substituted by 1–3 substituents selected from the group consisting of F, Cl, CF$_3$, (C$_1$–C$_4$)-alkyl or -alkoxy, and NR(10)R(11);

R(10) and R(11) are H or (C$_1$–C$_4$)-alkyl;

but where R(2) and R(3) cannot simultaneously be hydrogen, or a pharmaceutically tolerable salt thereof;

and L is a leaving group which can be easily nucleophilically substituted.

5. A method for treating arrhythmias, which comprises administering to a host in need thereof an effective amount of a compound of formula I as claimed in claim 1.

6. A method for treating or preventing cardiac infarct, which comprises administering to a host in need thereof an effective amount of a compound of formula I as claimed in claim 1.

7. A method for treating angina pectoris, which comprises administering to a host in need thereof an effective amount of a compound of formula I as claimed in claim 1.

8. A method for treating ischemic conditions, which comprises administering to a host in need thereof an effective amount of a compound of formula I as claimed in claim 1.

9. A method for treating diseases in which proliferation of fibroblasts is a primary or secondary cause, which comprises administering to a host in need thereof an effective amount of a compound of formula I as claimed in claim 1.

10. The method according to claim 7, wherein said disease is atherosclerosis, late complications of diabetes, a cancer or a fibrotic disease.

11. The method according to claim 10, wherein said fibrotic disease is pulmonary fibrosis, fibrosis of the liver or fibrosis of the kidneys.

12. A diagnostic agent for inhibiting a $Na^+/H^+$ exchanger and the diagnosing hypertension and proliferative disorders, which comprises an effective amount of a compound of formula I as claimed in claim 1 and a pharmaceutically acceptable carrier.

* * * * *

UNITED STATES PATENT AND TRADEMARK OFFICE
CERTIFICATE OF CORRECTION

PATENT NO. : 5,693,672
DATED : December 02, 1997
INVENTOR(S) : Andreas WEICHERT et al.

It is certified that error appears in the above-identified patent and that said Letters Patent is hereby corrected as shown below:

Claim 3, column 13, line 58, "$(C_1 14\ C_4)$-alkyl" should read --$(C_1-C_4)$-alkyl--.

Signed and Sealed this

Fourth Day of August, 1998

Attest:

BRUCE LEHMAN

*Attesting Officer*   *Commissioner of Patents and Trademarks*